United States Patent
Suzuki et al.

(10) Patent No.: US 8,524,263 B2
(45) Date of Patent: Sep. 3, 2013

(54) SHEET-LIKE COSMETIC

(75) Inventors: Kazunobu Suzuki, Yokahama (JP); Rie Yamamoto, Yokahama (JP); Kenji Ito, II, Yokahama (JP); Kazuhiko Fujiwara, Yokahama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 13/376,725

(22) PCT Filed: Aug. 18, 2010

(86) PCT No.: PCT/JP2010/063917
§ 371 (c)(1),
(2), (4) Date: Dec. 7, 2011

(87) PCT Pub. No.: WO2011/077779
PCT Pub. Date: Jun. 30, 2011

(65) Prior Publication Data
US 2012/0076844 A1    Mar. 29, 2012

(30) Foreign Application Priority Data
Dec. 21, 2009  (JP) ................. 2009-289267

(51) Int. Cl.
*A61K 8/02*   (2006.01)
*A61K 31/19*  (2006.01)

(52) U.S. Cl.
USPC .......................... 424/401; 514/557

(58) Field of Classification Search
None
See application file for complete search history.

(56) References Cited

U.S. PATENT DOCUMENTS

| | | | | |
|---|---|---|---|---|
| 5,620,694 | A * | 4/1997 | Girardot | 424/402 |
| 6,428,799 | B1 * | 8/2002 | Cen et al. | 424/402 |
| 2004/0018166 | A1 * | 1/2004 | Chen et al. | 424/70.16 |
| 2005/0013784 | A1 * | 1/2005 | Trigg et al. | 424/62 |

FOREIGN PATENT DOCUMENTS

| | | | |
|---|---|---|---|
| DE | 10033975 | A1 * | 1/2002 |
| JP | 6040886 | | 2/1994 |
| JP | 2000256168 | A | 9/2000 |
| JP | 2005120051 | A | 5/2005 |
| JP | 2005132828 | A | 5/2005 |
| JP | 2006-008615 | A | 1/2006 |
| JP | 20068630 | A | 1/2006 |
| JP | 2008100966 | A * | 5/2008 |
| JP | 2008-230994 | A | 10/2008 |

OTHER PUBLICATIONS

Raw Machine Translation of JP 2006-008615 translated on May 13, 2012.*
Raw Machine Translation of JP 2008-230994 translated on May 13, 2012.*
An English Translation of JP2008100966A was provided on Nov. 8, 2012.*
International Search Report issued on Sep. 28, 2010, in corresponding International Application No. PCT/JP2010/063917.
International Preliminary Report on Patentability, PCT/JP2010/063917 mailed Jul. 19, 2012, 6 pages—English.

* cited by examiner

*Primary Examiner* — Susan Tran
*Assistant Examiner* — Jessica Worsham
(74) *Attorney, Agent, or Firm* — Andrew F. Young, Esq.; Lackenbach Siegel, LLP

(57) ABSTRACT

The present invention is a sheet-like cosmetic produced by impregnating a non-woven fabric with a cosmetic comprising (A) 4-methoxysalicylic acid or a salt thereof and (B) a water soluble polysaccharide. It also provides a sheet-like cosmetic that additionally comprises (C) an oil component, (D) an alkyl-modified carboxyvinyl polymer, (E) a water soluble polymer other than said (B) and (D), and (F) hydroxylamine or a derivative thereof.

The object of the present invention is to improve the texture upon use, such as the stickiness and the friction, of a sheet-like cosmetic produced by impregnating a non-woven fabric with a cosmetic comprising 4-methoxysalicylic acid or a salt thereof.

14 Claims, No Drawings

SHEET-LIKE COSMETIC

CROSS REFERENCE TO A RELATED APPLICATIONS

This is a national stage patent application of co-pending PCT International application No. PCT/JP2010/063917, filed Aug. 18, 2010.

TECHNICAL FIELD

The present invention relates to a sheet-like cosmetic. More specifically, it relates to a sheet-like cosmetic produced by impregnating a non-woven fabric with a cosmetic comprising 4-methoxysalicylic acid or a salt thereof wherein improvements are made in the texture upon use, such as a stickiness or a friction caused by the 4-methoxysalicylic acid or a salt thereof, said sheet-like cosmetic being preferably used mainly as a face mask.

BACKGROUND ART

Alkoxysalicylic acid such as 4-methoxysalicylic acid is a prior art cosmetic ingredient as a whitening agent. Patent Document 1 discloses an external preparation that contains alkoxysalicylic acid as a whitening agent and it describes a lotion that combines 3-methoxysalicylic acid and a water soluble polysaccharide (sodium hyaluronate) (0042-0045). However, there is no investigation into suppression of the stickiness and friction due to 3-methoxysalicylic acid by adding a water soluble polysaccharide.

Patent Document 2 discloses a non-woven impregnated cosmetic containing a whitening agent and mentyl lactate, and it specifically discloses 4-methoxysalicylic acid as the whitening agent (0019). However, in this non-woven impregnated cosmetic, the problem of the stickiness and friction due to 4-methoxysalicylic acid is not necessarily solved sufficiently.

Patent Document 3 discloses that the stickiness and the friction are suppressed by adding a small amount of an oil component (0.01-3 wt %) to a liquid cosmetic comprising an alkoxysalicylic acid derivative. However, an oil component is required to suppress the stickiness and the friction and the amount to be added is limited, therefore the suppression of the stickiness and the friction is not sufficient and the texture upon use is also limited.

Patent Document 4 discloses an example (0020, Example 5) of an external preparation comprising 4-methoxysalicylic acid and alkyl-modified carboxyvinyl polymer. However, this Example does not sufficiently solve the problem of the stickiness and the friction arising from 4-methoxysalicylic acid.

As described thus far, a cosmetic comprising both 4-methoxysalicylic acid or a salt thereof and a water soluble polysaccharide is a conventional technology, but a sheet-like cosmetic that uses said cosmetic as the impregnating liquid of non-woven fabric has not been directly described.

Also, in the conventional technology, investigations have been conducted on the stickiness and the friction arising when a cosmetic comprising 4-methoxysalicylic acid or a salt thereof is directly applied on the skin and the cosmetic dries on the skin, but there has been no investigation on using a water soluble polysaccharide to reduce this stickiness and friction when a sheet-like cosmetic produced by impregnating a non-woven fabric with said cosmetic is applied on the skin.

PRIOR ART DOCUMENTS

Patent Documents

Patent Citation 1: JP 2722309 B2
Patent Citation 2: JP 2004-131388 A
Patent Citation 3: JP 2009-242326 A
Patent Citation 4: JP 2005-068115 A

SUMMARY OF INVENTION

Problem that Invention is to Solve

In view of the situation described above, the inventors carried out earnest research on the texture upon use of a sheet-like cosmetic produced by impregnating a non-woven fabric with a cosmetic comprising 4-methoxysalicylic acid or a salt thereof, and, as a result, discovered that, compared with applying said cosmetic directly on the skin, adding a water soluble polysaccharide to the sheet-like cosmetic results in the superior effect of reducing the stickiness and the friction due to 4-methoxysalicylic acid, thus completed the present invention.

The object of the present invention is to provide a sheet-like cosmetic that significantly improves the texture upon use (particularly the stickiness and the friction) of a sheet-like cosmetic produced by impregnating a non-woven fabric with a cosmetic comprising 4-methoxysalicylic acid or a salt thereof.

Technical Solution

That is, the present invention provides a sheet-like cosmetic produced by impregnating a non-woven fabric with a cosmetic comprising (A) 4-methoxysalicylic acid or a salt thereof and (B) a water soluble polysaccharide.

Also, the present invention provides the aforementioned sheet-like cosmetic wherein said (B) water soluble polysaccharide is one, two or more selected from hyaluronic acid or a salt thereof, acetylated hyaluronic acid or a salt thereof, and xanthan gum.

Furthermore, the present invention provides the aforementioned sheet-like cosmetic that additionally contains (C) an oil component.

Furthermore, the present invention provides the aforementioned sheet-like cosmetic that additionally contains (D) an alkyl-modified carboxyvinyl polymer.

Furthermore, the present invention provides the aforementioned sheet-like cosmetic that additionally contains (E) a water soluble polymer other than said (B) and (D).

Furthermore, the present invention provides the aforementioned sheet-like cosmetic that additionally contains (F) hydroxylamine or a derivative thereof.

Advantageous Effects

According to the present invention, a sheet-like cosmetic giving a superior texture upon use can be obtained by adding a water soluble polysaccharide to a sheet-like cosmetic produced by impregnating a non-woven fabric with a cosmetic comprising 4-methoxysalicylic acid or a salt thereof.

Furthermore, a sheet-like cosmetic giving an even superior texture upon use can be obtained by additionally using an oil component, alkyl-modified carboxyvinyl polymer, water soluble polymer, and hydroxyamine or a derivative thereof.

MODE FOR CARRYING OUT THE INVENTION (A) 4-Methoxysalicylic Acid or a Salt Thereof 4-methoxysalicylic acid is a prior art cosmetic ingredient and it is known to have a whitening effect. Selection of the salt of 4-methoxysalicylic acid is not limited in particular; examples include alkaline metal salts or alkaline earth metal salts such as a sodium salt, potassium salt, calcium salt, and magnesium salt, as well as an ammonium salt and amino acid salt.

The blend ratio of 4-methoxysalicylic acid or a salt thereof is usually 0.7-5.0 wt %, preferably 1.0-3.0 wt %, of the total amount of the cosmetic impregnating the non-woven fabric. If it is less than 0.7 wt % then a sufficient whitening effect is difficult to be achieved; if it is more than 5.0 wt % then the texture upon use, such as the stickiness, tends to be worsened.

(B) Water Soluble Polysaccharide

Selection of the water soluble polysaccharide that is additionally used with 4-methoxysalicylic acid and a salt thereof is not limited; examples include hyaluronic acid or a salt thereof, acetylated hyaluronic acid or a salt thereof, chondroitin sulfate or a salt thereof, xanthan gum, succinoglucane, quince seed, pectin, mannan, alginate, propylene glycol alginate, hydroxyethyl cellulose, and hydroxypropylmethyl cellulose. Particularly preferable are hyaluronic acid or a salt thereof, acetylated hyaluronic acid or a salt thereof, and xanthan gum; hyaluronic acid or a salt thereof and acetylated hyaluronic acid or a salt thereof are more preferable than xanthan gum. Also, it is more preferable to use two or more than just using one.

The addition of hyaluronic acid or a salt thereof, acetylated hyaluronic acid or a salt thereof, xanthan gum, etc. makes it possible to reduce the stickiness and the friction due to 4-methoxysalicylic acid or a salt thereof in a sheet-like cosmetic.

In the case of a sheet-like cosmetic produced by impregnating a non-woven fabric with a cosmetic comprising 4-methoxysalicylic acid or a salt thereof, there has been no investigation into a reduction in the stickiness and the friction due to 4-methoxysalicylic acid or a salt thereof by means of a water soluble polysaccharide such as hyaluronic acid or a salt thereof, acetylated hyaluronic acid or a salt thereof, and xanthan gum; the inventors were the first to investigate and achieve this effect.

The blend ratio of the water soluble polysaccharide is usually 0.001-3.0 wt % of the total amount of the cosmetic impregnating the non-woven fabric.

Specifically, the blend ratio of hyaluronic acid or a salt thereof and acetylated hyaluronic acid or a salt thereof is 0.001-3.0 wt %, preferably 0.005-1.0 wt %, of the total amount of the cosmetic impregnating the non-woven fabric.

The blend ratio of xanthan gum is 0.01-1.0 wt %, preferably 0.05-0.3 wt %, of the total amount of the cosmetic impregnating the non-woven fabric.

(C) Oil Component

Selection of the oil component that can be added to the present invention is not limited in particular; examples include liquid fats and oils, solid fats and oils, waxes, hydrocarbon oils, higher fatty acids, higher alcohols, ester oils, and silicone oils.

Examples of the liquid fats and oils include avocado oil, camellia oil, macadamia nut oil, corn oil, olive oil, rapeseed oil, sesame oil, wheat germ oil, sasanqua oil, castor oil, linseed oil, safflower oil, cotton seed oil, perilla oil, soybean oil, peanut oil, tea seed oil, Japanese nutmeg oil, rice bran oil, Chinese gimlet oil, Japan gimlet oil, jojoba oil, germ oil, and medowfoam oil.

Examples of the solid fats and oils include cacao butter, coconut oil, hydrogenated coconut oil, palm oil, palm kernel oil, Japanese core wax nucleus oil, Japanese core wax, and hydrogenated castor oil.

Examples of the waxes include beeswax, candelilla wax, carnauba wax, lanolin, liquid lanolin, sugar cane wax, lanolin fatty acid isopropyl ester, reduced lanolin, jojoba wax, hard lanolin, shellac wax, ceresin, and microcrystalline wax.

Examples of the hydrocarbon oils include liquid petrolatum, squalene, paraffin, squalene, and petrolatum.

Examples of the higher fatty acids include myristic acid, palmitic acid, stearic acid, behenic acid, oleic acid, undecylenic acid, isostearic acid, linolic acid, linoleic acid, eicosapentaenoic acid, and docosahexaenoic acid.

Examples of the higher alcohols include straight chain alcohols (for example, lauryl alcohol, cetyl alcohol, stearyl alcohol, behenyl alcohol, myristyl alcohol, oleyl alcohol, and cetostearyl alcohol) and branched chain alcohols (for example, mono stearyl glycerin ether (batyl alcohol), 2-decyltetradecynol, lanolin alcohol, cholesterol, phytosterol, hexyl dodecanol, isostearyl alcohol, and octyl dodecanol).

Examples of the ester oils include isopropyl myristate, cetyl octanoate, octyl dodecyl myristate, isopropyl palmitate, butyl stearate, hexyl laurate, myristyl myristate, decyl oleate, hexyl decyl dimethyl octanoate, cetyl lactate, myristyl lactate, lanolin acetate, isocetyl stearate, isocetyl isostearate, cholesteryl 12-hydroxystearate, di-2-ethylene glycol ethylhexanoate, dipentaerythritol fatty acid ester, n-alkylene glycol monoisostearate, neopentyl glycol dicaprate, diisostearyl malate, glyceryl di-2-heptylundecanoate, trimethylolpropane tri-2-ethyl hexanoate, trimethylolpropane triisostearate, tetra-2-pentaerythritol ethylhexanoate, glycerin tri2-ethylhexanoate, glyceryl trioctanoate, glycerin triisopalmitate, trimethylolpropane triisostearate, cetyl 2-ethyl hexanoate, 2-ethylhexyl palmitate, glycerin trimyristate, tri-2-heptyl undecanoic acid glyceride, methyl castor oil fatty acid, oleyl oleate, acetoglyceride, 2-heptylundecyl palmitate, diisobutyl adipate, 2-octyldodecyl N-lauroyl-L-glutamate, di-2-heptylundecyl adipate, ethyl laurate, di2-ethylhexyl sebacate, 2-hexyldecyl myristate, 2-hexyldecyl palmitate, 2-hexyldecyl adipate, diisopropyl sebacate, 2-ethylhexyl succinate, and triethyl citrate.

Examples of the silicone oils include chain polysiloxanes (for example, dimethylpolysiloxane, methylphenyl polysiloxane, and diphenyl polysiloxane); ring polysiloxanes (for example, octamethylcyclotetrasiloxane, decamethyl cyclopenta siloxane, and dodecamethyl cyclohexa siloxane), silicone resins forming a three-dimensional network structure, silicone rubbers, and various modified polysiloxanes (amino-modified polysiloxane, polyether-modified polysiloxane, alkyl-modified polysiloxane, and fluorine-modified polysiloxane).

Particularly preferable are squalane, liquid paraffin, hydrogenated polydecene, isododecane, isohexadecane, isostearic acid, stearyl alcohol, behenyl alcohol, triethylhexanoin, pentaerythrityl tetraethylhexanoate, dimethylpolysiloxane, methylphenylpolysiloxane, and decamethylcyclopentasiloxane.

The effect of adding the oil component is an improvement in the texture upon use, such as the freshness, absence of the friction, and the moisture.

The blend ratio of the oil component is 0.01-20.0 wt %, preferably 0.5-10.0 wt %, of the total amount of the cosmetic impregnating the non-woven fabric.

(D) Alkyl-Modified Carboxyvinyl Polymer

Selection of the alkyl-modified carboxyvinyl polymer that can be added to the present invention is not limited in particular; examples include an acrylic acid/alkyl methacrylate copolymer. Particularly preferable is (acrylic acid/alkyl acrylate (C10-30)) copolymer.

The effects of adding an alkyl-modified carboxyvinyl polymer are an improvement in the thickening properties, emulsification of the oil component, and an improvement in the texture upon use. Specific examples of alkyl-modified carboxyvinyl polymer include Pemulen TR-1, Pemulen TR-2, and Carbopol 1342 (from BF Goodrich).

The blend ratio of the alkyl-modified carboxyvinyl polymer is 0.01-2.0 wt %, preferably 0.05-0.5 wt %, of the total amount of the cosmetic impregnating the non-woven fabric.

(E) Water Soluble Polymer Other than Said (B) and (D)

Selection of the water soluble polymer other than said (B) and (D) is not limited in particular; examples include natural water soluble polymers, semisynthetic water soluble polymers, and synthetic water soluble polymers.

Particularly preferable are carboxyvinyl polymer, polyacrylate, polyacrylamide, and high polymer polyoxyethylene.

The effects of adding an water soluble polymer are an improvement in the thickening properties and an improvement in the texture upon use.

The blend ratio of the water soluble polymer is usually 0.01-3.0 wt %, preferably 0.05-1.0 wt %, of the total amount of the cosmetic impregnating the non-woven fabric.

(F) Hydroxyamine or a Derivative Thereof

Selection of the hydroxyamine or a derivative thereof that can be added to the present invention is not limited in particular; examples include triethanolamine, diethanolamine, monoethanolamine, triisopropanolamine, 2-amino-2-methyl-1-propanol, and 2-amino-2-methyl-1,3-propandiol, and 2-amino-2-hydroxymethyl-1,3-propandiol. Particularly preferable are 2-amino-2-methyl-1-propanol and 2-amino-2-methyl-1,3-propandiol.

The hydroxyamine or a derivative thereof is added as a neutralizer for the alkyl-modified carboxyvinyl polymer, the ionic water soluble polysaccharide, and the ionic water soluble polymer; the addition of this increases the freshing texture upon use.

The blend ratio of the hydroxylamine or a derivative thereof is 0.01-1.0 wt %, preferably 0.01-0.5 wt %, of the total amount of the cosmetic impregnating the non-woven fabric.

The sheet-like cosmetic of the present invention is prepared by impregnating a non-woven sheet with a cosmetic containing the aforementioned essential ingredients, by using a conventional method. Selection of the non-woven fabric to be impregnated is not limited in particular; a single layer or laminated layers of a single fiber or mixed fiber selected from natural fibers, regenerated fibers, and synthetic fibers such as cotton, pulp, rayon, polyethylene, polypropylene, polyethylene terephthalate, and nylon. Particularly preferable are laminated layers of a single fiber or mixed fiber selected from cotton, rayon, polyethylene terephthalate, and pulp.

Selection of the formulation of the cosmetic that impregnates the non-woven fabric is not limited in particular; it can be a solubilized system such as a lotion or an emulsified system such as an emulsion, essence, and cream.

The impregnation amount of the cosmetic that impregnates the non-woven fabric is not limited in particular and adjusted appropriately based on the properties of the non-woven fabric and the cosmetic; a preferable impregnation amount is 6-15 times the weight of the non-woven fabric.

The sheet-like cosmetic of the present invention is preferably used as a face mask product that is applied on the face.

In addition to the aforementioned essential ingredients, other ingredients used in cosmetics can be blended as necessary in the cosmetic that impregnates the non-woven sheet; examples include whitening agents other than 4-methoxysalicylic acid or a salt thereof, ultraviolet absorbents, surfactants, humectants, thickeners, alcohols, powder ingredients, coloring agents, pH adjusting agents, stabilizers, preservatives, perfumes, water, and various skin nutrients.

From the point of view of the moisture retaining effect of the cosmetic that impregnates the sheet-like cosmetic, it is preferable to add a humectant such as glycerin and butylene glycol.

EXAMPLES

The invention is described in detail through Examples below, but the invention shall not be limited to these implementations. The blend ratios in Examples are in wt % (mass-percentage) units unless specified otherwise.

Examples 1-7, Comparative Examples 1

Samples of a lotion having the composition shown in Table 1 were prepared. A panel of 10 specialists applied the samples directly on the face and separately applied a sheet-like cosmetic (face mask) prepared by impregnating a non-woven fabric (100% cotton, face-shaped, density 70 g/m$^2$, and the impregnation amount 9 times) on the face and peeled it off after 10 minutes, and evaluated both cases for the absence of the stickiness when the sample is about to dry and also the absence of the friction when the sample is about to dry.

For each test item, each specialist in the panel made an evaluation based on the following evaluation point criteria, and a four step evaluation scale was established using the total of the evaluation points. The results for both cases are shown in Tables 1.

<Evaluation Point Criteria>
5 points: Exceptionally superior
4 Points: Excellent.
3 points: Midway
2 point: Inferior
1 point: Very inferior
<Evaluation Criteria>
⊙: The total score is 40 points or higher.
○: The total score is 30-39 points.
Δ: The total score is 20-39 points.
X: The total score is 19 points or lower.

TABLE 1

| Ingredient names | Example 1 | Example 2 | Example 3 | Example 4 | Example 5 | Example 6 | Example 7 | Comparative example 1 |
|---|---|---|---|---|---|---|---|---|
| (A) Potassium 4-methoxysalicylate | 3.0 | 3.0 | 1.0 | 1.0 | 1.0 | 1.0 | 1.0 | 3.0 |
| (B) Sodium hyaluronate | 0.01 | — | 0.005 | — | — | — | — | — |
| (B) Sodium acetylated hyaluronate | — | — | — | 0.005 | — | — | — | — |
| (B) Xanthan gun | — | 0.1 | 0.05 | — | 0.1 | — | — | — |

TABLE 1-continued

| Ingredient names | | Example 1 | Example 2 | Example 3 | Example 4 | Example 5 | Example 6 | Example 7 | Comparative example 1 |
|---|---|---|---|---|---|---|---|---|---|
| (B) Succinoglucane | | — | — | — | — | — | 0.1 | — | — |
| (B) Hydroxyethyl cellulose | | — | — | — | — | — | — | 0.1 | — |
| Glycerin | | 1.0 | 1.0 | 1.0 | 1.0 | 1.0 | 1.0 | 1.0 | 1.0 |
| Ion-exchanged water | | Balance | Balance | Balance | Balance | Balance | Balance | Balance | Balance |
| Direct application | Absence of the stickiness | Δ | Δ | Δ | Δ | Δ | Δ | Δ | X |
|  | Absence of the friction | Δ | Δ | Δ | Δ | Δ | Δ | Δ | X |
| Applying impregnated non-woven fabric | Absence of the stickiness | ○ | ○ | ◎ | ○ | ○ | ○ | ○ | Δ |
|  | Absence of the friction | ◎ | ○ | ◎ | ◎ | ◎ | ○ | ○ | Δ |

The results shown in Table 1 indicate that a non-woven fabric impregnated with both the water soluble polysaccharide and potassium 4-methoxysalicylate applied on the face shows an improvement over direct application on the face in terms of the stickiness and the friction. It also indicates that sodium hyaluronate has a superior effect in reducing the friction, compared with xanthan gum. It also indicates that using sodium hyaluronate and xanthan gum jointly produces a superior texture upon use compared with using just one of them. It also indicates that sodium hyaluronate, sodium acetylated hyaluronate, and xanthan gum give a superior texture upon use, compared with the other water soluble polysaccharides.

Examples 8-15, Comparative Examples 2-5

Samples of lotions having the compositions shown in Table 2 and Table 3 were prepared. A sheet-like cosmetic (face mask) was prepared by using a conventional method to impregnate this cosmetic into a non-woven fabric (mixed fiber made of polyethylene terephthalate and cotton, density 80 g/m$^2$, impregnation amount 8 times).

A panel of 10 specialists applied the sheet-like cosmetic on the face and peeled it off after ten minutes, at which point they evaluated the freshness, absorption into the skin, the absence of the stickiness when the sample is about to dry, and also the absence of the friction when the sample is about to dry. For each test item, each specialist in the panel made an evaluation based on the following evaluation point criteria, and a four step evaluation scale was established using the total of the evaluation points. The results are also shown.

<Evaluation Point Criteria>

5 points: Exceptionally superior 4 points: Excellent.

3 points: Midway 2 point: Inferior 1 point: Very inferior

<Evaluation Criteria>

◎: The total score is 40 points or higher.

○: The total score is 30-39 points.

Δ: The total score is 20-39 points.

X: The total score is 19 points or lower.

TABLE 2

| Ingredient names | Example 8 | Example 9 | Example 10 | Example 11 | Example 12 | Example 13 | Example 14 | Example 15 |
|---|---|---|---|---|---|---|---|---|
| (A) Potassium 4-methoxysalicylate | 3.0 | 3.0 | 3.0 | 3.0 | 3.0 | 3.0 | 3.0 | 3.0 |
| (B) Sodium hyaluronate | 0.01 | 1.0 | — | — | — | 0.01 | — | — |
| (B) Xanthan gun | — | — | 0.1 | 1.0 | 0.1 | 0.1 | 0.1 | 0.1 |
| (C) Dimethylpolysiloxane *$^1$ | — | — | — | — | — | 1.0 | 1.0 | 1.0 |
| (C) Triethylhexanoin | — | — | — | — | 1.0 | 2.0 | 2.0 | 2.0 |
| (C) Squalane | — | — | — | — | 2.0 | 2.0 | 2.0 | 2.0 |
| (C) Liquid paraffin | — | — | — | — | — | 1.0 | 1.0 | 1.0 |
| Polyoxyethylene-hydrogenated castor oil | 0.3 | 0.3 | 0.3 | 0.3 | 0.3 | — | — | — |
| (D) (Acrylic acid/alkylacrylate (C10-30) copolymer *$^2$ | — | — | — | — | — | 0.1 | 0.1 | 0.1 |
| (E) Carboxyvinyl polymer | — | — | — | — | — | — | 0.2 | 0.2 |
| Potassium hydroxide | — | — | — | — | — | 0.03 | 0.07 | — |
| (F) 2-amino-2-methyl-1-propandiol | — | — | — | — | — | — | — | 0.1 |
| Glycerin | 3.0 | 3.0 | 3.0 | 3.0 | 3.0 | 3.0 | 3.0 | 3.0 |
| Butylene glycol | 5.0 | 5.0 | 5.0 | 5.0 | 5.0 | 5.0 | 5.0 | 5.0 |
| Citric acid | 0.02 | 0.02 | 0.02 | 0.02 | 0.02 | — | — | — |
| Sodiun citrate | 0.08 | 0.08 | 0.08 | 0.08 | 0.08 | — | — | — |
| Phenoxy ethanol | 0.3 | 0.3 | 0.3 | 0.3 | 0.3 | 0.3 | 0.3 | 0.3 |
| Perfume | 0.01 | 0.01 | 0.01 | 0.01 | 0.01 | 0.01 | 0.01 | 0.01 |
| Ion-exchanged water | Balance | Balance | Balance | Balance | Balance | Balance | Balance | Balance |
| Freshness | ○ | ○ | ○ | ○ | ◎ | ○ | ○ | ◎ |
| Absorption into the skin | ◎ | ○ | ◎ | ○ | ○ | ◎ | ◎ | ◎ |
| Absence of the stickiness | ○ | ○ | ○ | ○ | ◎ | ◎ | ◎ | ◎ |
| Absence of the friction | ○ | ◎ | ○ | ◎ | ◎ | ◎ | ◎ | ◎ |

*$^1$ KF-96A-6CS (from Shin-Etsu Chemical Co., Ltd.)

*$^2$ Pemulen TR-2 (from B F Goodrich)

TABLE 3

| Ingredient Names | Comparative example 2 | Comparative example 3 | Comparative example 4 | Comparative example 5 |
|---|---|---|---|---|
| (A) Potassium 4-methoxysalicylate | 3.0 | 3.0 | 3.0 | 3.0 |
| (B) Sodium hyaluronate | — | — | — | — |
| (B) Xanthan gum | — | — | — | — |
| (2) Dimethylpolysiloxane *[1] | — | — | — | 1.0 |
| (C) Triethylhexanoin | — | 1.0 | — | 2.0 |
| (C) Squalane | — | 2.0 | 10.0 | 2.0 |
| (C) Liquid paraffin | — | — | — | 1.0 |
| Polyoxyethylene-hydrogenated castor oil | 0.3 | 0.3 | — | — |
| (D) (Acrylic acid/alkyl acrylate (C10-30) copolymer *[2] | — | — | 0.5 | 0.1 |
| (E) Carboxyvinyl polymer | — | — | — | 0.2 |
| Potassium hydroxide | — | — | 0.05 | — |
| (F) 2-amino-2-methyl-1-propandiol | — | — | — | 0.1 |
| Glycerin | 3.0 | 3.0 | 3.0 | 3.0 |
| Butylene glycol | 5.0 | 5.0 | 5.0 | 5.0 |
| Citric acid | 0.02 | 0.02 | — | — |
| Sodium citrate | 0.08 | 0.08 | — | — |
| Edetate | 0.1 | 0.1 | 0.1 | 0.1 |
| Phenoxy ethanol | 0.3 | 0.3 | 0.3 | 0.3 |
| Perfume | 0.01 | 0.01 | 0.01 | 0.01 |
| Ion-exchanged water | Balance | Balance | Balance | Balance |
| Freshness | Δ | ○ | Δ | ○ |
| Absorption into the skin | ○ | ○ | ○ | ○ |
| Absence of the stickiness | x | Δ | x | ○ |
| Absence of the friction | Δ | Δ | x | Δ |

*[1] KF-96A-6CS (from Shin-Etsu Chemical Co., Ltd.)
*[2] Pemulen TR-2 (from B F Goodrich)

The aforementioned Table 2 and Table 3 indicate that a sheet-like cosmetic containing 4-methoxysalicylate that is superior in terms of the absence of the stickiness and the absence of the friction can be obtained by adding sodium hyaluronate and/or xanthan gum. It indicates that, by further adding an alkyl-modified carboxyvinyl polymer and hydroxyamine, a sheet-like cosmetic containing 4-methoxysalicylate that is also superior in terms of the freshness and spread on the skin can be obtained.

Other formulations of the sheet-like cosmetic are described below. Every Example is a sheet-like cosmetic that gives a superior texture upon use.

Example 16

| (Ingredient) | (wt %) |
|---|---|
| Ethanol | 10.0 |
| PPG-13 decyltetradeceth-24 | 0.3 |
| Methylparaben | 0.1 |
| Phenoxyethanol | 0.1 |
| Perfume | Appropriate amount |
| Glycerin | 2.0 |
| PEG/PPG-14/7 dimethyl ether | 3.0 |
| Dipropylene glycol | 1.0 |
| 1,3-butylene glycol | 5.0 |
| Potassium 4-methoxysalicylicate | 2.0 |
| Dipotassium glycyrrhizinate | 0.05 |
| Ethyl vitamin C | 0.3 |
| Sodium hyaluronate | 1.0 |
| Xanthan gum | 0.3 |
| Mannan | 0.1 |
| Citric acid | Appropriate amount |
| Sodium citrate | Appropriate amount |
| Edetate | Appropriate amount |
| Ion-exchanged water | Balance |

A sheet-like cosmetic (face mask) is obtained by impregnating this cosmetic into a non-woven fabric (mixed fiber made of polyethylene terephthalate and cotton, density 90 g/m$^2$). The impregnation amount of the cosmetic is 10 times the mass of the non-woven fabric.

Example 17

| (Ingredient) | (wt %) |
|---|---|
| Polyglyceryl diisostearate | 0.2 |
| PEG-60 hydrogenated castor oil | 0.2 |
| Triethylhexanoin | 0.3 |
| Methylparaben | 0.2 |
| Ethylparaben | 0.2 |
| Glycerin | 3.0 |
| 1,3-butylene glycol | 9.0 |
| Potassium 4-methoxysalicylicate | 2.0 |
| Sodium acetylated hyaluronate | 0.3 |
| Carrageenan | 0.05 |
| Citric acid | Appropriate amount |
| Sodium citrate | Appropriate amount |
| Edetate | Appropriate amount |
| Ion-exchanged water | Balance |

A sheet-like cosmetic (face mask) is obtained by impregnating the cosmetic of the aforementioned formulation into a non-woven fabric (100% cotton, density 40 g/m$^2$). The impregnation amount of the cosmetic is 6 times the mass of the non-woven fabric.

Example 18

| (Ingredient) | (wt %) |
|---|---|
| Ethanol | 5.0 |
| Dipropylene glycol | 1.0 |
| 1,3-butylene glycol | 0.6 |
| Polyethylene glycol 1000 | 1.0 |
| Polyoxyethylene methyl glucoside | 1.0 |
| Isostearic acid | 0.2 |
| Glyceryl tri-2-ethylhexanoate | 2 |
| Polyoxyethylene (30) phytosterol | 0.09 |
| Sorbitan sesquiisostearate | 0.03 |
| Potassium 4-methoxysalicylicate | 2.0 |
| Ascorbic acid glucoside | 1.0 |
| Succinoglucane | 0.1 |
| Quince seed | 0.5 |
| Sodium hyaluronate | 0.05 |
| Sodium acetylated hyaluronate | 0.01 |
| Citric acid | Appropriate amount |
| Sodium citrate | Appropriate amount |
| Edetate | Appropriate amount |
| Ion-exchanged water | Balance |

A sheet-like cosmetic (face mask) is obtained by impregnating the cosmetic of the aforementioned formulation into a non-woven fabric (mixed fiber made of polyethylene terephthalate and cotton, density 60 g/m²). The impregnation amount of the cosmetic is 10 times the mass of the non-woven fabric.

Example 19

| (Ingredient) | (wt %) |
|---|---|
| Decamethylcyclopentasiloxane | 3.0 |
| Dimethylpolysiloxane | 2.0 |
| (KF-96A-6CS from Shin-Etsu Chemical Co., Ltd.) | |
| Di (phytosteryl/2-octyldodecyl) N-lauroyl-L-glutaminate | 2.0 |
| Cetyl octanoate | 1.0 |
| (Acrylic acid/alkyl acrylate (C10-30) ) copolymer | 0.3 |
| Hydroxyethyl cellulose | 0.1 |
| Sodium polyacrylate | 0.2 |
| Polyvinyl alcohol | 0.1 |
| Glycerin | 10.0 |
| Propylene glycol | 5.0 |
| Locust bean gum | 0.2 |
| Sodium hyaluronate | 0.8 |
| Potassium 4-methoxysalicylicate | 1.5 |
| Tocopherol acetate | 0.5 |
| Nicotinic acid amide | 4.0 |
| 2-amino-2-methyl-1-propanol | 0.1 |
| Sodium metaphosphate | Appropriate amount |
| Ion-exchanged water | Balance |

A sheet-like cosmetic (face mask) is obtained by impregnating the cosmetic of the aforementioned formulation into a non-woven fabric (mixed fiber made of cotton, polyethylene terephthalate, and pulp, density 80 g/m²). The impregnation amount of the cosmetic is 15 times the mass of the non-woven fabric.

INDUSTRIAL APPLICABILITY

The sheet-like cosmetic of the present invention is a sheet-like cosmetic that gives a superior texture upon use and is preferably used mainly as an impregnated non-woven fabric face mask.

The invention claimed is:

1. A cosmetic produced by impregnating non-woven fabric with a cosmetic composition, said cosmetic comprising:
a sheet of non-woven fabric being impregnated with a fluid cosmetic composition,
said fluid cosmetic composition comprising:
(A) 0.7 to 5 wt % of 4-methoxysalicylic acid or a salt thereof;
(B) 0.001 to 0.3 wt % of hyaluronic acid or a salt thereof;
(C) 0.01 to 0.3 wt % xanthan gum; and
(D) water.

2. The cosmetic of claim 1, wherein an impregnation amount of said cosmetic composition to be impregnated into the non-woven fabric is 6-15 times the mass of the non-woven fabric.

3. The cosmetic of claim 1, wherein said cosmetic composition further comprises:
(E) an oil component; and
(F) an alkyl-modified carboxyvinyl polymer component.

4. The cosmetic of claim 2, wherein said cosmetic composition further comprises:
(E) an oil component; and
(F) an alkyl-modified carboxyvinyl polymer component.

5. The cosmetic of claim 3, wherein said cosmetic composition further comprises:
(G) 0.05 to 0.3 wt % acrylic acid/alkylacrylate co-polymer.

6. The cosmetic of claim 5, wherein said cosmetic composition further comprises (H) 0.01 to 0.5 wt % 2-amino-2-methyl-1,3-propanediol.

7. The cosmetic of claim 1, wherein said (B) component is 0.001 to 0.3 wt % acetylated hyaluronic acid or a salt thereof.

8. A face mask cosmetic sheet, said sheet comprising:
a sheet of non-woven fabric made of polyethylene terephthalate and cotton or 100% cotton or mixed fibers of cotton, polyethyleneterephthalate and pulp, being impregnated with a fluid cosmetic composition, said fluid cosmetic composition comprising a combination of:
(A) 0.7 to 5 wt % of 4-methoxysalicylic acid or a salt thereof;
(B) 0.001 to 0.3 wt % of hyaluronic acid or a salt thereof;
(C) 0.01 to 0.3 wt % xanthan gum; and
(D) water.

9. The face mask cosmetic sheet of claim 8, wherein the mass of said cosmetic composition is 6-15 times the mass of the non-woven fabric.

10. The face mask cosmetic sheet of claim 8, wherein said cosmetic composition further comprises:
(E) an oil component; and
(F) an alkyl-modified carboxyvinyl polymer component.

11. The face mask cosmetic sheet of claim 9, wherein said cosmetic composition further comprises:
(E) an oil component; and
(F) an alkyl-modified carboxyvinyl polymer component.

12. The face mask cosmetic sheet of claim 9, wherein said cosmetic composition further comprises:
(G) 0.05 to 0.3 wt % acrylic acid/alkylacrylate co-polymer.

13. The face mask cosmetic sheet of claim 12, wherein said cosmetic composition further comprises (H) 0.01 to 0.5 wt % 2-amino-2-methyl-1,3-propanediol.

14. The face mask cosmetic sheet of claim 8, wherein said (B) component is 0.001 to 0.3 wt % acetylated hyaluronic acid or a salt thereof.

* * * * *